(12) United States Patent
Hashimoto

(10) Patent No.: US 10,065,916 B2
(45) Date of Patent: Sep. 4, 2018

(54) METHOD FOR PRODUCING (METH)ACRYLATE

(71) Applicant: TOAGOSEI CO., LTD., Tokyo (JP)

(72) Inventor: Naoki Hashimoto, Aichi (JP)

(73) Assignee: TOAGOSEI CO., LTD, Tokyo (JP)

( * ) Notice: Subject to any disclaimer, the term of this patent is extended or adjusted under 35 U.S.C. 154(b) by 0 days.

(21) Appl. No.: 15/556,743

(22) PCT Filed: Mar. 3, 2016

(86) PCT No.: PCT/JP2016/056687
§ 371 (c)(1),
(2) Date: Sep. 8, 2017

(87) PCT Pub. No.: WO2016/143677
PCT Pub. Date: Sep. 15, 2016

(65) Prior Publication Data
US 2018/0105483 A1    Apr. 19, 2018

(30) Foreign Application Priority Data

Mar. 10, 2015    (JP) .................................. 2015-046655

(51) Int. Cl.
*C07C 67/00* (2006.01)
*C07C 67/02* (2006.01)
*B01J 31/22* (2006.01)

(52) U.S. Cl.
CPC ........... *C07C 67/02* (2013.01); *B01J 31/2226* (2013.01); *B01J 2231/49* (2013.01); *B01J 2531/26* (2013.01)

(58) Field of Classification Search
CPC .................................... C07C 67/02

USPC ........................................................ 560/217
See application file for complete search history.

(56) References Cited

U.S. PATENT DOCUMENTS

| 2013/0072712 A1 | 3/2013 | Kawamoto et al. |
| 2017/0204044 A1 | 7/2017 | Hashimoto et al. |

FOREIGN PATENT DOCUMENTS

| JP | 2001316328 A | * | 11/2001 |
| JP | 2001316328 A |   | 11/2001 |
| JP | 2003171345 A | * | 6/2003 |
| JP | 2003171345 A |   | 6/2003 |
| JP | 2003190819 A |   | 7/2003 |
| JP | 2003286226 A |   | 10/2003 |

(Continued)

OTHER PUBLICATIONS

Munshi et al., Journal of Molecular Catalysis A: Chemical, Apr. 24, 2014, vol. 391, pp. 144-149. (Year: 2014).*

(Continued)

*Primary Examiner* — Deborah D Carr
(74) *Attorney, Agent, or Firm* — Norris McLaughlin & Marcus PA

(57) ABSTRACT

A method for producing a (meth)acrylate comprises transesterification reaction of an alcohol and a monofunctional (meth) acrylate with catalysts in combination being cyclic tertiary amines having an azabicyclo structure and compounds containing zinc, separating a solid that contains the catalysts from a reaction product containing a (meth)acrylate, and producing a (meth)acrylate by transesterification reaction of an alcohol and a monofunctional (meth)acrylate, while using the recovered solid catalyst.

9 Claims, 1 Drawing Sheet

REACTION INTERMEDIATE

(56) References Cited

FOREIGN PATENT DOCUMENTS

| | | | | |
|---|---|---|---|---|
| JP | 4656351 B2 | 3/2011 | | |
| WO | 2011/148903 A1 | 12/2011 | | |
| WO | WO-2011148903 A1 * | 12/2011 | ............. | C07C 67/31 |
| WO | 2015/159611 A1 | 10/2015 | | |

OTHER PUBLICATIONS

International Search Report dated May 20, 2016, dated May 31, 2016.

English translation of International Search Report dated May 20, 2016, dated May 31, 2016.

* cited by examiner

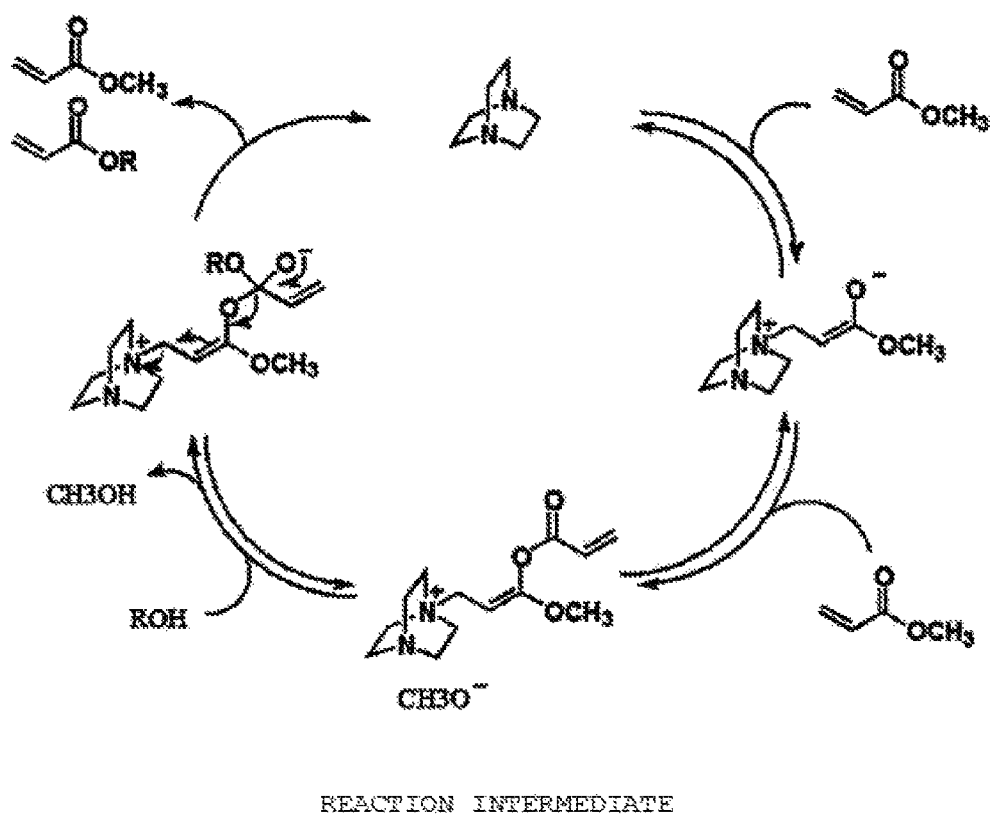
REACTION INTERMEDIATE

METHOD FOR PRODUCING (METH)ACRYLATE

This application is a 371 application of PCT/JP2016/056687 filed Mar. 3, 2016, which claims foreign priority benefits under 35 U.S.C. § 119 of Japanese Application No. 2015-046655 filed Mar. 10, 2015, the disclosures of each of which are incorporated by reference herein in their entirety.

TECHNICAL FIELD

The present invention relates to a method for producing a (meth) acrylate. More specifically, it relates to a method for producing a (meth) acrylate, which includes subjecting an alcohol and a monofunctional (meth) acrylate to a transesterification reaction to obtain a (meth) acrylate. In particular, it relates to the recovery and reuse of a catalyst to be used.

BACKGROUND ART (Meth) acrylates are cured by being irradiated with active energy rays such as ultraviolet rays and electron beams or by being heated, and they are thus used in large quantities as a cross linking component of blended materials such as paints, inks, adhesives, optical lenses, fillers, and molding materials or a reactive diluent component.

Inparticular,polyfunctional (meth) acrylates having three or more (meth) acryloyl groups are used in large quantities as a blending component of hard coat paints since the cured products thereof exhibit high hardness and excellent abrasion resistance.

As such polyfunctional (meth) acrylates, trimethylolpropane tri (meth) acrylate, glycerol tri (meth) acrylate, pentaerythritol tri (meth) acrylate, pentaerythritol tetra (meth) acrylate, ditrimethylolpropane tetra (meth) acrylate, dipentaerythritol tetra (meth) acrylate, dipentaerythritol penta (meth) acrylate, dipentaerythritol hexa (meth) acrylate, tripentaerythritol octa (meth) acrylate, and the like are known.

These (meth) acrylates are produced by an esterification reaction of the corresponding alcohol with the corresponding (meth) acrylic acid or a transesterification reaction.

In the production of (meth) acrylates by an esterification reaction, sulfuric acid and sulfonic acid such as p-toluenesulfonic acid or methanesulfonic acid are used as a catalyst. However, it is required to conduct extraction and washing with an aqueous alkali solution in order to remove the sulfonic acid from the reaction crude product obtained after completion of the esterification reaction, and the step is complicated and the productivity remarkably decreases. In addition, there is a problem that the yield decreases by saponification of a part of the target (meth) acrylate in the extraction operation.

Meanwhile, in the production of (meth) acrylates by a transesterification reaction, the reaction can also proceed without using sulfonic acid. For example, a method in which an organotin compound is used as a catalyst (see Patent Literature 1), a method in which a zinc compound and an organophosphorus compound are concurrently used as a catalyst (see Patent Literature 2), a method in which a gelled styrene-based polymer or a gelled polysiloxane-based polymer which has a phosphonium structure having a structure to coordinate a metal compound containing a specific metal atom is used as a catalyst (see Patent Literature 3), and the like are known. In these methods, it is required to recover and reuse the catalyst from the viewpoint of economic efficiency and environmental burden.

In the production of (meth) acrylates by a transesterification reaction, a method in which an organotin compound is used as a catalyst (see Patent Literature 1) is disclosed as a method for recovering and reusing a catalyst. However, in Patent Literature 1, it is required to further conduct the dehydration operation after the extraction operation by warm water is conducted plural times in order to recover the catalyst, and the step is complicated and the productivity remarkably decreases.

In addition, in Patent Literature 3, it is described that the catalyst can be separated through filtration after the reaction is completed. However, it is required to prepare a polymer having a special structure through a complicated step, and it is thus hard to say that this method is an economically advantageous production method.

CITATION LIST

Patent Literature

Patent Literature 1: JP 2003-190819 A
Patent Literature 2: JP 4656351 B1
Patent Literature 3: JP 2003-286226 A

SUMMARY OF INVENTION

Technical Problem

The present invention has been made in view of the situation described above, it is a method for recovering a catalyst in the production of a (meth) acrylate and using the recovered catalyst in the production of a (meth) acrylate again, and an object thereof is to obtain a (meth) acrylate at a favorable yield by an economically advantageous method in which the catalyst is recovered and reused by an extremely simple method without requiring a complicated recovery operation and preparation of a special polymer.

Solution to Problem

The present inventors have conducted intensive investigations to solve the above problems. As a result, it has been found out that it is possible to separate and recover a catalyst A and/or a catalyst B as a solid from the reaction product after the transesterification reaction by an extremely simple operation by concurrently using the following catalyst A and catalyst B when a (meth) acrylate is produced by a transesterification reaction of an alcohol with a monofunctional (meth) acrylate. Furthermore, it has been found out that it is possible to obtain a (meth) acrylate at a favorable yield by an economically advantageous method without a decrease in catalyst performance even when a transesterification reaction of an alcohol with a monofunctional (meth) acrylate is conducted by using the separated and recovered solid as a catalyst or a part of a catalyst, thereby completing the present invention.

In other words, the present invention is a method for producing a (meth) acrylate, which includes the following steps.

(Reaction step 1) a step of producing a (meth) acrylate by subjecting an alcohol and a monofunctional (meth) acrylate to a transesterification reaction using the following catalyst A and the following catalyst B concurrently.

Catalyst A: one or more kinds of compounds selected from the group consisting of a cyclic tertiary amine having an azabicyclo structure, a salt of the cyclic tertiary amine, and a complex of the cyclic tertiary amine.

Catalyst B: one or more kinds of compounds selected from the group consisting of a compound containing zinc.

(Catalyst recovery step) a step of separating a solid containing the catalyst A and/or the catalyst B from a reaction product which is obtained in the reaction step 1 and contains a (meth) acrylate.

(Reaction step 2) a step of producing a (meth) acrylate by subjecting an alcohol and a monofunctional (meth) acrylate to a transesterification reaction using the solid which is recovered in the catalyst recovery step and contains the catalyst A and/or the catalyst B as a catalyst or a part of a catalyst.

Incidentally, in the present invention, the "(meth) acrylate" means the target (meth) acrylate contained in the reaction product obtained in the reaction step 1 or the reaction step 2. The resulting (meth) acrylate is monofunctional, bifunctional, or polyfunctional depending on the number of hydroxylgroupsinthealcoholtobeused. Inthepresentinvention, the "monofunctional (meth) acrylate" means a (meth) acrylate to be used as a raw material.

Advantageous Effects of Invention

According to the production method of the present invention, it is possible to recover a catalyst by a simple method and to reuse the catalyst without causing a decrease in catalyst performance as well as to obtain a (meth) acrylate at a favorable yield. It is possible to suitably use the (meth) acrylate obtained by the production method of the present invention in various kinds of industrial applications as a crosslinking component of blended materials such as paints, inks, adhesives, optical lenses, fillers, and molding materials or a reactive diluent component.

BRIEF DESCRIPTION OF DRAWINGS

FIG. 1 is a schematic diagram illustrating the reaction mechanism in the method for producing a (meth) acrylate according to the present invention.

DESCRIPTION OF EMBODIMENTS

The present invention is a method for producing a (meth) acrylate, which includes the following steps.

(Reaction step 1) a step of producing a (meth) acrylate by subjecting an alcohol and a monofunctional (meth) acrylate to a transesterification reaction using the following catalyst A and the following catalyst B concurrently.

Catalyst A: one or more kinds of compounds selected from the group consisting of a cyclic tertiary amine having an azabicyclo structure, a salt of the cyclic tertiary amine, and a complex of the cyclic tertiary amine.

Catalyst B: one or more kinds of compounds selected from the group consisting of a compound containing zinc.

(Catalyst recovery step) a step of separating a solid containing the catalyst A and/or the catalyst B from a reaction product which is obtained in the reaction step 1 and contains a (meth) acrylate.

(Reaction step 2) a step of producing a (meth) acrylate by subjecting an alcohol and a monofunctional (meth) acrylate to a transesterification reaction using the solid which is recovered in the catalyst recovery step and contains the catalyst A and/or the catalyst B as a catalyst or a part of a catalyst.

Hereinafter, the present invention will be described in detail.

First, the reaction step 1 will be described.

In the reaction step 1 in the production method of the present invention, the alcohol to be used as a raw material is an aliphatic alcohol, an alicyclic alcohol, an aromatic alcohol, a polyhydric alcohol ether, and the like which have at least one or more alcoholic hydroxyl groups in the molecule. The alcohol may have other functional groups or bonds, for example, a phenolic hydroxyl group, a ketone group, an acyl group, an aldehyde group, a thiol group, an amino group, an imino group, a cyano group, a nitro group, an ether bond, an ester bond, a carbonate bond, an amide bond, an imide bond, a peptide bond, a urethane bond, an acetal bond, a hemiacetal bond, and a hemiketal bond in the molecule.

Specific examples of the monohydric alcohol having one alcoholic hydroxyl group may include a monohydric alcohol having an ether bond in the molecule such as ethylene glycol monomethyl ether, diethylene glycol monomethyl ether, diethylene glycol monoethyl ether, triethylene glycol monomethyl ether, tetraethylene glycol monomethyl ether, polyethylene glycol monomethyl ether, dipropylene glycol monomethyl ether, tripropylene glycol monobutyl ether, polypropylene glycol monoethyl ether, 1,6-hexanediol monomethyl ether, 1,6-hexanediol monoethyl ether, tetramethylene glycol monomethyl ether, tetramethylene glycol monoethyl ether, polytetramethylene glycol monomethyl ether, polytetramethylene glycol monoethyl ether, glycidol, 2-(2-chloroethoxy)ethanol, 2-(2-dimethylaminoethoxy)ethanol, or an alkylene oxide modified product of 2-ethylhexyl alcohol; a monohydric alcohol having a vinyl group and an ether bond in the molecule such as 2-hydroxyethyl vinyl ether (another name: ethylene glycol monovinyl ether), 3-hydroxypropyl vinyl ether, 2-hydroxypropyl vinyl ether, 2-hydroxyisopropyl vinyl ether, 4-hydroxybutyl vinyl ether, 3-hydroxybutyl vinyl ether, 2-hydroxybutyl vinyl ether, 3-hydroxyisobutyl vinyl ether, 2-hydroxyisobutyl vinyl ether, 1-methyl-3-hydroxypropyl vinyl ether, 1-methyl-2-hydroxypropyl vinyl ether, 1-hydroxymethylpropyl vinyl ether, 4-hydroxycyclohexyl vinyl ether, 1,6-hexanediol monovinyl ether, tetramethylene glycol monovinyl ether, polytetramethylene glycol monovinyl ether 1,4-cyclohexanedimethanol monovinyl ether, 1,3-cyclohexanedimethanol monovinyl ether, 1,2-cyclohexanedimethanolmonovinylether, isosorbidemonovinyl ether,p-xyleneglycolmonovinylether, m-xyleneglycolmonovinyl ether, o-xylene glycol monovinyl ether, diethylene glycol monovinyl ether, triethylene glycol monovinyl ether, tetraethylene glycol monovinyl ether, pentaethylene glycol monovinyl ether, oligoethylene glycol monovinyl ether, polyethylene glycol monovinyl ether, dipropylene glycol monovinyl ether, tripropylene glycol monovinyl ether, tetrapropylene glycol monovinyl ether, pentapropylene glycol monovinyl ether, oligopropylene glycol monovinyl ether, polypropylene glycol monovinyl ether, or ethylene glycol-propylene glycol copolymer monovinyl ether; a monohydric alcohol having a ring structure such as tricyclo[5.2.1.0$^{2,6}$]decenol (another name: hydroxydicyclopentadiene), tricyclo[5.2.1.0$^{2,6}$]decanol, tricyclo[5.2.1.0$^{2,6}$]decenyloxyethanol, tricyclo[5.2.1.0$^{2,6}$]decanyloxyethanol, tricyclo[5.2.1.0$^{2,6}$]decenyloxypropanol, tricyclo[5.2.1.0$^{2,6}$]decanyloxypropanol, tricyclo[5.2.1.0$^{2,6}$]decenyloxyethoxyethanol, tricyclo[5.2.1.0$^{2,6}$]decanyloxyethoxyethanol, 4-hydroxy-2,2,6,6-tetramethylpiperidine, 4-hydroxy-1,2,2,6,6-pentamethylpiperidine, oxetanylmethanol, tetrahydrofurfuryl alcohol, tetrahydropyranyl alcohol, 1,4- cyclohexanedimethanol monomethyl ether, 1,3-cyclohexanedimethanol monomethyl ether, 1,2-cyclohexanedimethanol monomethyl ether, isosorbide monomethyl ether, isosorbide monoethyl ether, 2,3-O-sec-butylidene glycerol, 5-ethyl-5-(hydroxylmethyl)-1,3-dioxane, α-hydroxy-γ-butyrolactone, glycerol 1,2-carbonate, 1,3-dioxolan-4-yl-methanol, 2,2-dimethyl-1,3-dioxolane-4-methanol, β-hydroxy-γ-butyrolactone, α-hydroxymethyl-γ-butyrolactone, or β-hydroxymethyl-γ-butyrolactone; and an alcohol having an aromatic ring such as benzyl alcohol, phenoxyethanol, phenoxypropanol, p-xylene glycol monomethyl ether, m-xylene glycol monomethyl ether, o-xylene glycol monomethyl ether, an alkylene oxide modified product of phenol, an alkylene oxide modified product of o-phenylphenol, an alkylene oxide modified product of p-cumylphenol, or an alkylene oxide modified product of nonylphenol.

Specific examples of the dihydric alcohol having two alcoholic hydroxyl groups may include ethylene glycol, diethylene glycol, triethylene glycol, polyethylene glycol, propylene glycol, trimethylene glycol, dipropylene glycol, tripropylene glycol, polypropylene glycol, butanediol, pentanediol, hexanediol, heptanediol, nonanediol, neopentyl glycol, cyclohexanediol, cyclohexanedimethanol, dioxane glycol, N-methyldiethanolamine, N-ethyldiethanolamine, N-butyldiethanolamine, N-tert-butyldiethanolamine, N-lauryldiethanolamine, stearyldiethanolamine, N-phenyldiethanolamine, m-tolyldiethanolamine, p-tolyldiethanolamine, N,N'-bis(2-hydroxypropyl)aniline, N-nitrosodiethanolamine, N-(2-hydroxyethyl)lactamide, N,N'-bis(2-hydroxyethyl)oxamide, 3-morpholino-1,2-propanediol, 2,6-pyridinedimethanol, 3-(dimethylamino)-1,2-propanediol, 3-(diethylamino)-1,2-propanediol, alloxanthine dihydrate, (+)-N,N,N',N'-tetramethyl-L-tartaric acid diamide, (−)-N,N,N',N'-tetramethyl-D-tartaric acid diamide, N-propyl-N-(2,3-dihydroxypropyl) perfluoro-n-octylsulfonamide, thymidine, chloramphenicol, thiamphenicol, D-erythronolactone, methyl 4,6-O-benzylidene-α-D-glucopyranoside, phenyl 4,6-O-benzylidene-1-thio-β-D-glucopyranoside, 1,2:5,6-di-O-isopropylidene-D-mannitol, 1,2-O-isopropylidene-α-D-xylofuranose, 2,6-di-O-palmitoyl-L-ascorbic acid, isosorbide, and alkylene oxide adducts thereof, and further alkylene oxide adducts of compounds having a phenolic hydroxyl group such as hydroquinone, bisphenol A, bisphenol AP, bisphenol AF, bisphenol B, bisphenol BP, bisphenol C, bisphenol E, bisphenol F, bisphenol G, bisphenol M, bisphenol S, thiobisphenol, bisphenol P, bisphenol PH, bisphenol TMC, and bisphenol Z, and alcohols having a carbonate bond such as polycarbonatediol.

Specific examples of the trihydric alcohol having three alcoholic hydroxyl groups may include trimethylolethane, trimethylolpropane, glycerin, tris(2-hydroxyethyl) isocyanurate, hexanetriol, octanetriol, decanetriol, triethanolamine, triisopropanolamine, 1-[bis(2-hydroxyethyl)amino]-2-propanol, D-panthenol, DL-panthenol, uridine, 5-methyluridine, cytidine, inosine, adenosine, leucomycin A3, leucomycin A4, leucomycin A6, leucomycin A8, clindamycin hydrochloride monohydrate, prednisolone, methyl β-D-arabinopyranoside, methyl β-L-fucopyranoside, methyl α-L-fucopyranoside, D-galactar, 4-methoxyphenyl 3-O-allyl-β-D-galactopyranoside, 4-methoxyphenyl 3-O-benzyl-β-D-galactopyranoside, 1,6-anhydro-β-D-glucose, α-chloralose, β-chloralose, 4,6-O-ethylidene-α-D-glucopyranose, D-glucal, 1,2-O-isopropylidene-α-D-glucofuranose, D-glucurono-6,3-lactone, 2-deoxy-D-ribose, methyl β-D-ribofuranoside, D-(+)-ribono-1,4-lactone, methyl-β-D-xylopyranoside, 6-O-palmitoyl-L-ascorbic acid, 6-O-stearoyl-L-ascorbic acid, 3-O-ethyl-L-ascorbic acid, and alkylene oxide adducts thereof.

Specific examples of the tetrahydric alcohol having four alcoholic hydroxyl groups may include ditrimethylolethane, ditrimethylolpropane, diglycerin, pentaerythritol, N,N,N',N'-tetrakis (2-hydroxyethyl) butanediamide, N,N,N',N'-tetrakis (2-hydroxypropyl) butanediamide, N,N,N',N'-tetrakis (2-hydroxyethyl) hexanediamide, N,N,N',N'-tetrakis (2-hydroxypropyl) hexanediamide, N,N,N',N'-tetrakis (2-hydroxyethyl) ethylenediamine, N,N,N',N'-tetrakis (2-hydroxypropyl) ethylenediamine, N-hexanoyl-D-glucosamine, N-valeryl-D-glucosamine, N-trifluoroacetyl-D-glucosamine, N-benzoyl-D-glucosamine, 5-acetamido-N,N'-bis (2,3-dihydroxypropyl)-2,4,6-triiodoisoph thalamide,spiramycin,clarithromycin,leucomycin A1, eucomycin A5, leucomycin A7, leucomycin A9, leucomycin A13, lincomycin hydrochloride monohydrate, diazolidinyl urea, D-(−)-arabinose, DL-arabinose, L-(+)-arabinose, meso-erythritol, D-(+)-fucose, L-(−)-fucose, allyl α-D-galactopyranoside, methyl β-D-galactopyranoside, methyl α-D-galactopyranoside monohydrate, 4-methoxyphenyl β-D-galactopyranoside, 2-nitrophenyl β-D-galactopyranoside, 4-nitrophenyl α-D-galactopyranoside, 4-nitrophenyl β-D-galactopyranoside, phenyl β-D-galactopyranoside, N-acetyl-D-galactosamine hydrate, D-(+)-galactosamine hydrochloride, arbutin, 2-deoxy-D-glucose, esculin 1.5hydrate, D-(+)-glucono-1,5-lactone, D-glucuronamide, helicin, methyl α-D-glucopyranoside, methyl β-D-glucopyranoside 0.5 hydrate, 4-methoxyphenyl β-D-glucopyranoside, 4-nitrophenyl β-D-glucopyranoside monohydrate, 4-nitrophenyl α-D-glucopyranoside, nonyl β-D-glucopyranoside, n-octyl β-D-glucopyranoside, phenyl β-D-glucopyranoside hydrate, phlorizin hydrate, Piceid, puerarin, N-acetyl-D-glucosamine, N-benzoyl-D-glucosamine, D-(+)-glucosamine hydrochloride, N-hexanoyl-D-glucosamine, N-valeryl-D-glucosamine, L-(+)-gulonic acid γ-lactone, D-(−)-lyxose, L-(+)-lyxose, 3,4-O-isopropylidene-D-mannitol, methyl α-D-mannopyranoside, D-mannono-1,4-lactone, 4-methoxyphenyl α-D-mannopyranoside, N-acetyl-D-mannosamine monohydrate, D-(−)-ribose, L-ribose, D-(+)-xylose, DL-xylose, L-(−)-xylose, D-araboascorbic acid, L-ascorbic acid, L-threitol, and alkylene oxide adducts thereof.

Specific examples of the pentahydric alcohol having five alcoholic hydroxyl groups may include tritrimethylolethane, tritrimethylolpropane, triglycerol, bis (2-hydroxyethyl) aminotris (hydroxymethyl) methane, bis (2-hydroxypropyl) aminotris (hydroxymethyl) methane, N,N,N',N'',N''-pentakis (2-hydroxyethyl) diethylenetriamine, N,N,N',N'',N''-pentakis (2-hydroxypropyl) diethylenetriamine, miglitol, erythromycin, azithromycin dihydrate, D-(+)-arabitol, DL-arabitol, L-(−)-arabitol, D-(−)-fructose, L-(+)-fructose, D-(+)-galactose, L-(−)-galactose, β-D-glucose, D-(+)-glucose, L-(−)-glucose, D-glucose diethylmercaptal, salicin, L-gulose, D-(+)-mannose, L-(−)-mannose, ribitol, L-(−)-sorbose, D-tagatose, xylitol, sucralose, glyceryl ascorbate, and alkylene oxide adducts thereof.

Specific examples of the polyhydric alcohol having six or more alcoholic hydroxyl groups may include polytrimethylolethane, polytrimethylolpropane, polyglycerin, dipentaerythritol, tripentaerythritol, polypentaerythritol, iohexol, galactitol, D-sorbitol, L-sorbitol, myo-inositol, scyllo-inositol, D-mannitol, L-mannitol, icariin, amygdalin, D-(+)-cellobiose, diosmine, 2-O-α-D-glucopyranosyl-L-ascorbic acid, hesperidin, D-(+)-lactose monohydrate, lactulose, D-(+)-maltose monohydrate, D-(+)-melibiose monohydrate, methyl hesperidin, maltitol, naringin hydrate, neohesperidin dihydrochalcone hydrate, palatinose hydrate, rutin hydrate, D-(+)-sucrose, stevioside, D-(+)-turanose, D-(+)-trehalose (anhydrous), D-(+)-trehalose dihydrate, D-(+)-melezitose hydrate, D-(+)-raffinose pentahydrate, rebaudioside A, stachyose, α-cyclodextrin, β-cyclodextrin, γ-cyclodextrin, starch, polyvinyl alcohol, and alkylene oxide adducts thereof.

In the reaction step 1 in the production method of the present invention, these alcohols can be used singly or in arbitrary combination of two or more kinds thereof. Among these alcohols, polyhydric alcohols having three or more alcoholic hydroxyl groups are preferable, and particularly, trimethylolethane, trimethylolpropane, glycerin, an alkylene oxide adduct of glycerin, tris (2-hydroxyethyl) isocyanurate, triethanolamine, ditrimethylolethane, ditrimethylolpropane, diglycerin, an alkylene oxide adduct of diglycerin, pentaerythritol, an alkylene oxide adduct of pentaerythritol, xylitol, dipentaerythritol, an alkylene oxide adduct of dipentaerythritol, D-sorbitol, and polyglycerin are preferable. Incidentally, in a case in which there are hydrates or solvates of these alcohols, the hydrates and solvates thereof can also be used as an alcohol in the production method of the present invention.

In the reaction step 1 in the production method of the present invention, the monofunctional (meth) acrylate to be used as a raw material is a compound having one (meth) acryloyl group in the molecule, and examples thereof may include a compound represented by the following general formula (1).

[Chemical formula 1]

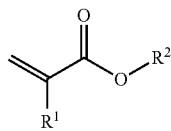

(1)

In the formula, $R^1$ represents a hydrogen atom or a methyl group. $R^2$ represents an organic group having from 1 to 50 carbon atoms.

Specific examples of $R^2$ in the general formula (1) may include a methyl group, an ethyl group, a n- or i-propyl group, a n-, i-, or t-butyl group, a n-, s-, or t-amyl group, a neopentyl group, a n-, s-, or t-hexyl group, a n-, s-, or t-heptyl group, a n-, s-, or t-octyl group, a 2-ethylhexyl group, a capryl group, a nonyl group, a decyl group, a undecyl group, a lauryl group, a tridecyl group, a myristyl group, a pentadecyl group, a cetyl group, a heptadecyl group, a stearyl group, a nonadecyl group, an aralkyl group, a seryl group, a myricyl group, a melissyl group, a vinyl group, an allyl group, a methallyl group, a crotyl group, a 1,1-dimethyl-2-propenyl group, a 2-methylbutenyl group, a 3-methyl-2-butenyl group, a 3-methyl-3-butenyl group, a 2-methyl-3-butenyl group, a butenyl group, a pentenyl group, a hexenyl group, a heptenyl group, an octenyl group, a nonenyl group, a decenyl group, an undecenyl group, a dodecenyl group, a tridecenyl group, a tetradecenyl group, a pentadecenyl group, a hexadecenyl group, a heptadecenyl group, an oleyl group, a linole group, a linolen group, a cyclopentyl group, a cyclopentylmethyl group, a cyclohexyl group, a cyclohexylmethyl group, a 4-methylcyclohexyl group, a 4-t-butylcyclohexyl group, a tricyclodecanyl group, an isobornyl group, an adamantyl group, a dicyclopentenyl group, a dicyclopentenyl group, a phenyl group, a methyl- phenyl group, a dimethylphenyl group, a trimethylphenyl group, a 4-t-butylphenyl group, a benzyl group, a diphenylmethyl group, a diphenylethyl group, a triphenylmethyl group, a cinnamyl group, a naphthyl group, an anthranyl group, a methoxyethyl group, a methoxyethoxyethyl group, a methoxyethoxyethyl group, a 3-methoxybutyl group, an ethoxyethyl group, an ethoxyethoxyethyl group, a cyclopentoxyethyl group, a cyclohexyloxyethyl group, a cyclopentoxyethoxyethyl group, a cyclohexyloxyethoxyethyl group, a dicyclopentenyloxyethyl group, a phenoxyethyl group, a phenoxyethoxyethyl group, a glycidyl group, a β-methylglycidyl group, a β-ethylglycidyl group, a 3,4-epoxycyclohexylmethyl group, a 2-oxetanemethyl group, a 3-methyl-3-oxetanemethyl group, a 3-ethyl-3-oxetanemethyl group, a tetrahydrofuranyl group, a tetrahydrofurfuryl group, a tetrahydropyranyl group, a dioxazolanyl group, a dioxanyl group, a N,N-dimethylaminoethyl group, a N,N-diethylaminoethyl group, aN,N-dimethylaminopropylgroup, aN,N-diethylaminopropylgroup, a N-benzyl-N-methylaminoethyl group, and a N-benzyl-N-methylaminopropyl group.

In the reaction step 1 in the production method of the present invention, these monofunctional (meth) acrylates can be used singly or in arbitrary combination of two or more kinds thereof. Among these monofunctional (meth) acrylates, methyl acrylate, ethyl acrylate, n-butyl acrylate, i-butyl acrylate, 2-ethylhexyl acrylate, 2-methoxyethyl acrylate, and 2-dimethylaminoethyl acrylate are preferable. In particular, methyl acrylate, ethyl acrylate, n-butyl acrylate, i-butyl acrylate, and 2-methoxyethyl acrylate which exhibit favorable reactivity to most alcohols and are easily available are preferable. Furthermore, 2-methoxyethyl acrylate which promotes the dissolution of alcohol and exhibits significantly favorable reactivity is more preferable.

In the reaction step 1 in the production method of the present invention, the proportion of the monofunctional (meth) acrylate used to the alcohol used is not particularly limited, but the monofunctional (meth) acrylate is used preferably at from 0.4 to 10.0 moles and more preferably at from 0.6 to 5.0 moles with respect to 1 mole of hydroxyl group in the alcohol. Side reactions increase when the amount of the monofunctional (meth) acrylate used is less than 0.4 mole. In addition, the amount of (meth) acrylate generated is small and the productivity deteriorates when the amount of the monofunctional (meth) acrylate used is more than 10.0 moles.

The reaction step 1 in the production method of the present invention can be conducted without using a solvent, but a solvent may be used if necessary. Specific examples of the solvent may include a hydrocarbon such as n-hexane, cyclohexane, methylcyclohexane, n-heptane, n-octane, n-nonane, n-decane, benzene, toluene, xylene, ethylbenzene, diethylbenzene, isopropylbenzene, amylbenzene, diamylbenzene, triamylbenzene, dodecylbenzene, didodecylbenzene, amyltoluene, isopropyltoluene, decalin, or tetralin; an ether such as diethyl ether, dipropyl ether, diisopropyl ether, dibutyl ether, diamyl ether, diethyl acetal, dihexyl acetal, t-butyl methyl ether, cyclopentyl methyl ether, tetrahydrofuran, tetrahydropyran, trioxane, dioxane, anisole, diphenyl ether, dimethylcellosolve, diglyme, triglyme, or tetraglyme; a crown ether such as 18-crown-6; an alcohol such as methanol, ethanol, n-propanol, i-propanol, n-butanol, i-butanol, t-butanol, ethylene glycol, 2-methoxyethanol, or glycerin; an ester such as methyl benzoate and γ-butyrolactone; a ketone such as acetone, methyl ethyl ketone, methyl isobutyl ketone, cyclohexanone, acetophenone, or benzophenone; a sulfone such as sulfolane; a sulfoxide such as dimethylsulfoxide; a carbonate compound such as dimethyl carbonate, diethyl carbonate, ethylene carbonate, propylene carbonate, or 1,2-butylene carbonate; a urea or a derivative thereof; a phosphine oxide such as tributylphosphine oxide; an ionic liquid such as an imidazolium salt, a piperidinium salt, or a pyridinium salt; silicone oil, and water. Among these solvents, a hydrocarbon, an ether, an alcohol, a carbonate compound, and an ionic liquid are preferable. These solvents may be used singly, or two or more kinds thereof may be arbitrarily combined and used as a mixed solvent.

In the reaction step 1 in the production method of the present invention, the catalyst A is one or more kinds of compounds selected from the group consisting of a cyclic tertiary amine having an azabicyclo structure, a salt of the cyclic tertiary amine, and a complex of the cyclic tertiary amine.

Specific examples of the cyclic tertiary amine having an azabicyclo structure or a salt thereof or a complex thereof may include 1-azabicyclo[1,1,0]butane, 1,3-diazabicyclo[1,1,0]butane, 1-azabicyclo[2,1,0]heptane, 1,3-diazabicyclo[2,1,0]heptane, 1,4-diazabicyclo[2,1,0]heptane, 1-azabicyclo[2,2,0]hexane, 1,3-diazabicyclo[2,2,0]hexane, 1-azabicyclo[2,1,1]hexane, 1,3-diazabicyclo[2,1,1]hexane, 1-azabicyclo[2,2,1]heptane, 1,3-diazabicyclo[2,2,1]heptane, 1,4-diazabicyclo[2,2,1]heptane, 1-azabicyclo[3,2,0]heptane, 1,3-diazabicyclo[3,2,0]heptane, 1,4-diazabicyclo[3,2,0]heptane, 1,6-diazabicyclo[3,2,0]heptane, 1,3-diazabicyclo[2,2,2]octane, 1-azabicyclo[3,2,1]octane, 1,3-diazabicyclo[3,2,1]octane, 1,4-diazabicyclo[3,2,1]octane, 1,5-diazabicyclo[3,2,1]octane, 1,6-diazabicyclo[3,2,1]octane, 1-azabicyclo[4,1,1]octane, 1,3-diazabicyclo[4,1,1]octane, 1,4-diazabicyclo[4,1,1]octane, 1,5-diazabicyclo[4,1,1]octane, 1,6-diazabicyclo[4,1,1]octane, 1,7-diazabicyclo[4,1,1]octane, 1-azabicyclo[4,2,0]octane, 1,3-diazabicyclo[4,2,0]octane, 1,4-diazabicyclo[4,2,0]octane, 1,5-diazabicyclo[4,2,0]octane, 1,7-diazabicyclo[4,2,0]octane, 1-azabicyclo[3,3,1]nonane, 1,3-diazabicyclo[3,3,1]nonane, 1,4-diazabicyclo[3,3,1]nonane, 1,5-diazabicyclo[3,3,1]nonane, 1-azabicyclo[3,2,2]nonane, 1,3-diazabicyclo[3,2,2]nonane, 1,4-diazabicyclo[3,2,2]nonane, 1,5-diazabicyclo[3,2,2]nonane, 1,6-diazabicyclo[3,2,2]nonane, 1,8-diazabicyclo[3,2,2]nonane, 1-azabicyclo[4,3,0]nonane, 1,3-diazabicyclo[4,3,0]nonane, 1,4-diazabicyclo[4,3,0]nonane, 1,5-diazabicyclo[4,3,0]nonane, 1,6-diazabicyclo[4,3,0]nonane, 1,7-diazabicyclo[4,3,0]nonane, 1,8-diazabicyclo[4,3,0]nonane, 1-azabicyclo[4,2,1]nonane, 1,3-diazabicyclo[4,2,1]nonane, 1,4-diazabicyclo[4,2,1]nonane, 1,5-diazabicyclo[4,2,1]nonane, 1,6-diazabicyclo[4,2,1]nonane, 1,7-diazabicyclo[4,2,1]nonane, 1-azabicyclo[5,2,0]nonane, 1,3-diazabicyclo[5,2,0]nonane, 1,4-diazabicyclo[5,2,0]nonane, 1,5-diazabicyclo[5,2,0]nonane, 1,6-diazabicyclo[5,2,0]nonane, 1,7-diazabicyclo[5,2,0]nonane, 1,8-diazabicyclo[5,2,0]nonane, 1-azabicyclo[5,1,1]nonane, 1,3-diazabicyclo[5,1,1]nonane, 1,4-diazabicyclo[5,1,1]nonane, 1,5-diazabicyclo[5,1,1]nonane, 1,6-diazabicyclo[5,1,1]nonane, 1,7-diazabicyclo[5,1,1]nonane, 1-azabicyclo[6,1,0]nonane, 1,3-diazabicyclo[6,1,0]nonane, 1,4-diazabicyclo[6,1,0]nonane, 1,5-diazabicyclo[6,1,0]nonane, 1,6-diazabicyclo[6,1,0]nonane, 1,7-diazabicyclo[6,1,0]nonane, 1,8-diazabicyclo[6,1,0]nonane, 1-azabicyclo[7,1,0]decane, 1,9-diazabicyclo[7,1,0]decane, 1-azabicyclo[6,2,0]decane, 1,8-diazabicyclo[6,2,0]decane, 1-azabicyclo[6,1,1]decane, 1,8-diazabicyclo[6,1,1]decane, 1-azabicyclo[5,3,0]decane, 1,7-diazabicyclo[5,3,0]decane, 1-azabicyclo[5,2,1]decane, 1,7-diazabicyclo[5,2,1]decane, 1-azabicyclo[4,3,1]decane, 1,6-diazabicyclo[4,3,1]decane, 1-azabicyclo[4,2,2]decane, 1,6-diazabicyclo[4,2,2]decane, 1-azabicyclo[5,4,0]undecane, 1,7-diazabicyclo[5,4,0]undecane, 1-azabicyclo[5,3,1]undecane, 1,7-diazabicyclo[5,3,1]undecane, 1-azabicyclo[5,2,2]undecane, 1,7-diazabicyclo[5,2,2]undecane, 1-azabicyclo[4,4,1]undecane, 1,7-diazabicyclo[4,4,1]undecane, 1-azabicyclo[4,3,2]undecane, 1,7-diazabicyclo[4,3,2]undecane, 1-azabicyclo[3,3,0]octane, 1-azabicyclo[4,3,0]nonane, quinuclidine, lupinane, lupinine, quinolizidine, 3-hydroxyquinuclidine, 3-quinuclidinone, quincorine, quincoridine, cinchonidine, cinchonine, quinidine, quinine, cupreine, ibogaine, swainsonine, castanospermine, mianserin, mirtazapine, canadine, Tröger's base, 1-azabicyclo[2,2,2]octane-3-carboxylic acid, triethylenediamine (another name: DABCO), 2-(hydroxymethyl)triethylenediamine, hexamethylenetetramine, 3-quinolizinone hydrochloride, 3-chloro-1-azabicyclo[2,2,2]octane hydrochloride, cinchonidine dihydrochloride, cinchonine hydrochloride hydrate, cinchonidine sulfate dihydrate, hydroquinidine hydrochloride, cinchonine sulfate dihydrate, quinine hydrochloride dihydrate, quinine sulfate dihydrate, quinine phosphate, quinidine sulfate dihydrate, mianserine hydrochloride, 1,1'-(butane-1,4-diyl)bis[4-aza-1-azoniabicyclo[2,2,2]octane]dibromide,1,1'-(decane-1,10-diyl)bis[4-aza-1-azoniabicyclo[2,2,2]octane]dibromide, bis(trimethylaluminum)-1,4-diazabicyclo[2,2,2]octane adduct, bismuthine, quinuclidine hydrochloride, 3-quinuclidinone hydrochloride, 3-hydroxyquinuclidine hydrochloride, DABCO hydrochloride, 2-(hydroxymethyl)triethylenediamine hydrochloride, quinuclidine acetate, 3-quinuclidinone acetate, 3-hydroxyquinuclidine acetate, DABCO acetate, 2-(hydroxymethyl)triethylenediamine acetate, quinuclidine acrylate, 3-quinuclidinone acrylate, 3-hydroxyquinuclidine acrylate, DABCO acrylate, and 2-(hydroxymethyl)triethylenediamine acrylate.

In the reaction step 1 of the production method of the present invention, these catalysts A can be used singly or in arbitrary combination of two of more kinds thereof. Among these catalysts A, quinuclidine, 3-quinuclidinone,3-hydroxyquinuclidine,DABCO, and 2-(hydroxymethyl) triethylenediamine are preferable, and particularly 3-hydroxyquinuclidine, DABCO, and 2-(hydroxymethyl) triethylenediamine which exhibit favorable reactivity to most alcohols and are easily available are preferable.

In the reaction step 1 in the production method of the present invention, the amount of the catalyst A used is not particularly limited, but the catalyst A is used preferably at from 0.0001 to 0.5 mole and still more preferably at from 0.0005 to 0.2 mole with respect to 1 mole of hydroxyl group in the alcohol. The amount of target (meth) acrylate generated is small when the amount of the catalyst A used is less than 0.0001 mole, and the amount of by-products increases and the coloration of the reaction liquid increases so that the purification step after completion of the reaction is complicated when the amount of the catalyst A used is more than 0.5 mole.

In the reaction step 1 in the production method of the present invention, the catalyst B is one or more kinds of compounds selected from the group consisting of a compound containing zinc, and examples thereof may include a compound which contains a zinc salt of an organic acid and is represented by the following general formula (2):

[Chemical formula 2]

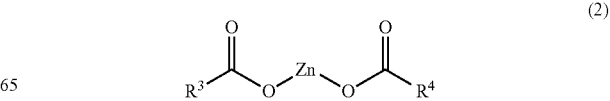

(2)

(in the formula, $R^3$ and $R^4$ may be the same as or different from each other, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent. However, $R^3$ and $R^4$ do not have a halogen atom such as fluorine or chlorine);

a compound which contains a zinc diketone enolate and is represented by the following general formula (3):

[Chemical formula 3]

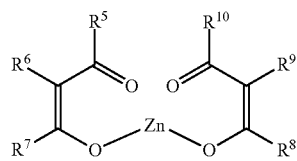

(3)

(in the formula, $R^5$, $R^6$, $R^7$, $R^8$, $R^9$, and R may be the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent. $R^6$ and $R^9$ may be a hydrogen atom); and zinc oxalate.

Specific examples of the compound which contains zinc and is represented by the general formula (2) may include zinc acetate, zinc acetate dihydrate, zinc propionate, zinc octylate, zinc neodecanoate, zinc laurate, zinc myristate, zinc stearate, zinc cyclohexanebutyrate, zinc 2-ethylhexanoate, zinc benzoate, zinc t-butylbenzoate, zinc salicylate, zinc naphthenate, zinc acrylate, and zinc methacrylate. Incidentally, in a case in which there are hydrates, solvates, or complexes with the catalyst A of these compounds containing zinc, the hydrates, the solvates, and the complexes with the catalyst A can also be used as the catalyst B in the production method of the present invention.

Specific examples of the compound which contains zinc and is represented by the general formula (3) may include zinc acetylacetonate, zinc acetylacetonate hydrate, zinc bis (2, 6-dimethyl-3, 5-heptanedionato), zinc bis (2,2,6,6-tetramethyl-3,5-heptanedionato), and zinc bis (5,5-dimethyl-2,4-hexanedionato). Incidentally, in a case in which there are hydrates, solvates, or complexes with the catalyst A of these compounds containing zinc, the hydrates, the solvates, and the complexes with the catalyst A can also be used as the catalyst B in the production method of the present invention.

As the zinc salt of an organic acid and the zinc diketone enolate in the catalyst B, the compounds described above can be directly used, but these compounds can also be generated in the reaction system and used. Examples thereof may include a method in which other zinc compounds such as metal zinc, zinc oxide, zinc hydroxide, zinc chloride, and zinc nitrate are used as a raw material and these zinc compounds are reacted with an organic acid in the case of a zinc salt of an organic acid and a method in which these zinc compounds are reacted with 1,3-diketone in the case of zinc diketone enolate.

In the reaction step 1 in the production method of the present invention, these catalysts B can be used singly or in arbitrary combination of two or more kinds thereof. Among these catalysts B, zinc acetate, zinc propionate, zinc acrylate, zinc methacrylate, and zinc acetylacetonate are preferable. In particular, zinc acetate, zinc acrylate, and zinc acetylacetonate which exhibit favorable reactivity to most alcohols and are easily available are preferable.

In the reaction step 1 in the production method of the present invention, the amount of the catalyst B used is not particularly limited, but the catalyst B is used preferably at from 0.0001 to 0.5 mole and still more preferably at from 0.0005 to 0.2 mole with respect to 1 mole of hydroxyl group in the alcohol. The amount of the target (meth) acrylate generated is small when the amount of the catalyst B used is less than 0.0001 mole, and the amount of by-products increases and the color tone of the reaction liquid deteriorates so that the purification step after completion of the reaction is complicated when the amount of the catalyst B used is more than 0.5 mole.

In the reaction step 1 in the production method of the present invention, the proportion of the catalyst A used to the catalyst B used is not particularly limited, but the catalyst A is used preferably at from 0.005 to 10.0 moles and still more preferably at from 0.05 to 5.0 moles with respect to 1 mole of the catalyst B. The amount of the target (meth) acrylate generated is small when the proportion of the catalyst A used to the catalyst B used is less than 0.005 mole, and the amount of by-products increases and the color tone of the reaction liquid deteriorates so that the purification step after completion of the reaction is complicated when the proportion is more than 10.0 moles.

In the reaction step 1 in the production method of the present invention, as the catalyst A and the catalyst B to be concurrently used, a combination in which the catalyst A is DABCO and the catalyst B is zinc acetate and/or zinc acrylate is the most preferable. This combination can be suitably used in various kinds of industrial applications in which the color tone is regarded as important since excellent color tone is exhibited after completion of the reaction as well as a (meth) acrylate is obtained at a favorable yield by this combination. Furthermore, this combination is economically advantageous since it is a relatively inexpensively available catalyst.

In the reaction step 1 in the production method of the present invention, it is presumed that the transesterification reaction proceeds by the reaction mechanism illustrated in FIG. 1. First, the electron density on the carbonyl oxygen atom increases as the catalyst A is added to the carbon at the β-position of the monofunctional (meth) acrylate, and the reaction intermediate illustrated in FIG. 1 is generated as this further attacks the carbonyl carbon of another monofunctional (meth) acrylate. It is presumed that the target (meth) acrylate is generated as this intermediate undergoes the transesterification reaction with the alcohol thereafter. At this time, it is presumed that the catalyst B exhibiting Lewis acidity promotes the reaction mechanism illustrated in FIG. 1 by activating the (meth) acryloyl group.

In the reaction step 1 in the production method of the present invention, the catalyst A and the catalyst B to be used may be added from the beginning or the middle of the above reaction. In addition, the desired amount of the catalyst A and the catalyst B to be used may be added at once or dividedly. In addition, the catalyst A and/or the catalyst B may be added after being dissolved in a solvent in the case of a solid.

In the reaction step 1 in the production method of the present invention, the reaction temperature is preferably from 40 to 180° C. and particularly preferably from 60 to 160° C. The reaction rate is significantly slow when the reaction temperature is lower than 40° C., and thermal polymerization of the (meth) acryloyl group takes place or the color tone of the reaction liquid deteriorates so that the purification step after completion of the reaction is complicated when the reaction temperature exceeds 180° C.

In the reaction step 1 in the production method of the present invention, the reaction pressure is not particularly limited as long as it can maintain a predetermined reaction temperature, and the reaction may be conducted in a reduced pressure state or a pressurized state. The reaction pressure is usually from 0.000001 to 10 MPa (absolute pressure).

In the reaction step 1 in the production method of the present invention, a monohydric alcohol derived from the monofunctional (meth) acrylate used as a raw material is generated as a by-product as the transesterification reaction proceeds. The monohydric alcohol may be allowed to coexist in the reaction system, but it is possible to further promote the advance of transesterification reaction by discharging the monohydric alcohol out of the reaction system.

In the reaction step 1 in the production method of the present invention, an inert gas such as argon, helium, nitrogen, or carbon dioxide gas may be introduced into the system for the purpose of maintaining the color tone of the reaction liquid favorably. In addition, an oxygen-containing gas may be introduced into the system for the purpose of preventing polymerization of the (meth) acryloyl group. Specific examples of the oxygen-containing gas may include air, a mixed gas of oxygen with nitrogen, and a mixed gas of oxygen with helium. As a method for introducing the oxygen-containing gas, there is a method in which the oxygen-containing gas is dissolved in or blown (so-called bubbling) into the reaction liquid.

In the reaction step 1 in the production method of the present invention, it is preferable to add a polymerization inhibitor into the system for the purpose of preventing polymerization of the (meth) acryloyl group. Specific examples of the polymerization inhibitor may include an organic polymerization inhibitor such as hydroquinone, tert-butylhydroquinone, hydroquinone monomethyl ether, 2,6-di-tert-butyl-4-methylphenol, 2,4,6-tri-tert-butylphenol, 4-tert-butylcatechol, benzoquinone, phenothiazine, N-nitroso-N-phenylhydroxylamine ammonium, 2,2,6, 6-tetramethylpiperidine-1-oxyl, or 4-hydroxy-2,2,6,6-tetramethylpiperidine-1-oxyl; an inorganic polymerization inhibitor such as copper chloride, copper sulfate, or iron sulfate; an organic salt-based polymerization inhibitor such as copper dibutyl-dithiocarbamate or N-nitroso-N-phenylhydroxylamine aluminum salt. The polymerization inhibitor may be added singly or in arbitrary combination of two or more kinds thereof. In addition, the polymerization inhibitor may be added from the beginning or the middle of the reaction. Furthermore, the desired amount of the polymerization inhibitor to be used may be added at once or dividedly. The polymerization inhibitor may be continuously added via the rectifying column. The amount of the polymerization inhibitor added is preferably from 5 to 30,000 ppm by mass and more preferably from 25 to 10,000 ppm by mass in the reaction liquid. The effect of inhibiting polymerization is insufficient when the amount of the polymerization inhibitor added is less than 5 ppm by mass, and the color tone of the reaction liquid deteriorates or the curing rate of the resulting (meth) acrylate decreases so that the purification step after completion of the reaction is complicated when the amount of the polymerization inhibitor added is more than 30,000 ppm by mass.

The reaction time in the reaction step 1 in the production method of the present invention varies depending on the kind and amount of catalyst used, the reaction temperature, the reaction pressure, and the like, but it is usually from 0.1 to 150 hours and preferably from 0.5 to 80 hours.

The reaction step 1 in the production method of the present invention can be carried out by any method of a batch method, a semi-batch method, or a continuous method. As an example of the batch method, an alcohol, a monofunctional (meth) acrylate, a catalyst, and a polymerization inhibitor are charged into a reactor and the mixture is stirred at a predetermined temperature while allowing an oxygen-containing gas to bubble in the reaction liquid. Thereafter, a monohydric alcohol derived from the monofunctional (meth) acrylate used as a raw material is generated as a by-product as the transesterification reaction proceeds. It is possible to generate the target (meth) acrylate by taking out the monohydric alcohol from the reactor at a predetermined pressure.

The high-purity target (meth) acrylate can be obtained by subjecting the reaction product obtained in the reaction step 1 in the production method of the present invention to the separation and purification operation in which a crystallization operation such as cooling crystallization or concentrating crystallization; a filtration operation such as pressure filtration, suction filtration, or centrifugal filtration; a distillation operation such as single distillation, fractional distillation, molecular distillation, or steam distillation; an extraction operation such as solid-liquid extraction and liquid-liquid extraction; decantation; and the like are combined. A solvent may be used in the separation and purification operation. In addition, a neutralizing agent for neutralizing the catalyst and/or the polymerization inhibitor used in the present invention or an adsorbent for adsorbing and removing the catalyst and/or the polymerization inhibitor, an acid and/or an alkali for decomposing or removing the by-products, activated carbon for improving the color tone, diatomaceous earth for improving the filtration efficiency and filtration rate, and the like may be used.

Next, the catalyst recovery step will be described.

The catalyst recovery step in the production method of the present invention is a step of separating a solid containing the catalyst A and/or the catalyst B from the reaction product obtained in the reaction step 1. The separation method is not particularly limited, but examples thereof may include separation and purification operations such as a crystallization operation such as cooling crystallization or concentrating crystallization; a filtration operation such as pressure filtration, suction filtration, or centrifugal filtration; a distillation operation such as single distillation, fractional distillation, molecular distillation, or steam distillation; an extraction operation such as solid-liquid extraction or liquid-liquid extraction; and decantation. These may be conducted singly or in arbitrary combination of two or more kinds thereof. Among these separation and purification operations, a filtration operation, solid-liquid extraction, and decantation are preferable, and particularly a filtration operation of the simplest operation is more preferable.

In the catalyst recovery step in the production method of the present invention, the solid means a substance collected on the filter as a residue after charging the reaction product obtained in the reaction step 1 into a filtering device equipped with a filter and subjecting the reaction product to the filtration operation.

The catalyst recovery step in the production method of the present invention can be carried out without using a solvent, but a solvent may be used if necessary. The same solvent as that in the reaction step 1 can be used, and the monofunctional (meth) acrylate of a raw material in the reaction step 1 can be used as a solvent. These solvents may be used singly or two or more kinds thereof may be arbitrarily combined and used as a mixed solvent.

The temperature for carrying out the catalyst recovery step in the production method of the present invention is preferably from −30° C. to 150° C. The target (meth) acrylate precipitates and the separation operation thereof from the solid containing the catalyst A and/or the catalyst B is complicated in some cases when the reaction temperature is lower than −30° C. Thermal polymerization of the (meth) acryloyl group takes place or the color tone of the reaction product deteriorates when the recovered catalyst is used in the reaction step 2 in some cases when the temperature exceeds 150° C.

The pressure for carrying out the catalyst recovery step in the production method of the present invention is not particularly limited as long as it can maintain a predetermined reaction temperature, and the catalyst recovery step may be carried out in a reduced pressure state or a pressurized state. The pressure is usually from 0.000001 to 10 MPa (absolute pressure).

In the catalyst recovery step in the production method of the present invention, an inert gas such as argon, helium, nitrogen, or carbon dioxide gas may be introduced into the system for the purpose of maintaining the color tone of the reaction liquid favorably. In addition, an oxygen-containing gas may be introduced into the system for the purpose of preventing polymerization of the (meth) acryloyl group. Specific examples of the oxygen-containing gas may include air, a mixed gas of oxygen with nitrogen, and a mixed gas of oxygen with helium. Examples of the method for introducing the gas may include a method in which the gas is blown (so-called bubbling) into the reaction product and a method in which the gas is introduced into the gas phase portion during the filtration operation such as pressure filtration or suction filtration.

In the catalyst recovery step in the production method of the present invention, a polymerization inhibitor may be added into the system for the purpose of preventing polymerization of the (meth) acryloyl group. The same polymerization inhibitor as that in the reaction step 1 can be used, and the polymerization inhibitor may be used singly or in arbitrary combination of two or more kinds thereof.

The time for carrying out the catalyst recovery step in the production method of the present invention is not particularly limited, but it is usually from 0.1 to 100 hours and preferably from 0.5 to 70 hours.

The catalyst recovery step in the production method of the present invention can be carried out by any method of a batch method, a semi-batch method, or a continuous method. As an example of the batch method, the reaction product obtained in the reaction step 1 is charged into a batch type pressurized filtering device equipped with a filter at the bottom from the top, an oxygen-containing gas is introduced into the gas phase portion to raise the pressure in the filtering device, and the liquid portion is then taken out from the extraction tube at the bottom of the filtering device via the filter. This makes it possible to easily separate and recover the solid containing the catalyst A and/or the catalyst B collected on the filter.

The solid which contains the catalyst A and/or the catalyst B and is separated and recovered in the catalyst recovery step in the production method of the present invention may be used in the reaction step 2 as it is, but it maybe used in the reaction step 2 after being rinsed with a solvent or being subjected to a drying treatment such as heat drying or vacuum drying.

Next, the reaction step 2 will be described.

In the reaction step 2 in the production method of the present invention, the same alcohol, the same monofunctional (meth) acrylate, and the same solvent as those in the reaction step 1 can be used. Preferred alcohols, preferred monofunctional (meth) acrylates, preferred solvents, preferred proportions of these used, and the like are also the same as those in the reaction step 1.

In the reaction step 2 in the production method of the present invention, a solid which contains the catalyst A and the catalyst B and is separated and recovered in the catalyst recovery step is used as a catalyst, or the solid containing the catalyst A and/or the catalyst B is used as a part of the catalyst. The reaction step 2 may be carried out by adding a new catalyst A and/or a new catalyst B which have not undergone the catalyst recovery step. The catalyst A and the catalyst B which can be used are the same as those in the reaction step 1, and the preferred catalyst A, the preferred catalyst B, the preferred proportion of these used, and the preferred adding method of these are also the same as those in the reaction step 1. As the catalyst A and/or the catalyst B, the recovered catalyst undergone the catalyst recovery step is used preferably at 10% by mass or more, more preferably at 40% by mass or more, and particularly preferably at 60% by mass or more.

The reaction step 2 in the production method of the present invention can be carried out at the same reaction temperature and the same reaction pressure for the same reaction time as those in the reaction step 1. The preferred reaction temperature, the preferred reaction pressure, and the preferable reaction time are also the same as those in the reaction step 1. In addition, the monohydric alcohol generated as a by-product as the transesterification reaction proceeds may be left to coexist in the reaction system, or the advance of transesterification reaction may be promoted by discharging the monohydric alcohol out of the reaction system in the same manner as in the reaction step 1.

In the reaction step 2 in the production method of the present invention, a gas may be introduced into the system or a polymerization inhibitor may be added in the same manner as in the reaction step 1. The kind of gas that can be used, the kind of polymerization inhibitor, the kind and amount of preferred polymerization inhibitor added, and the adding method of preferred polymerization inhibitor are also the same as those in the reaction step 1.

The reaction step 2 in the production method of the present invention can be carried out by any method of a batch method, a semi-batch method, or a continuous method in the same manner as in the reaction step 1. In addition, the high-purity target (meth) acrylate can be obtained by subjecting the reaction product to the same separation and purification operation as that in the reaction step 1. In the separation and purification operation, a solvent may be used, and a neutralizing agent for neutralizing the catalyst and/or the polymerization inhibitor used in the present invention or an adsorbent for adsorbing and removing the catalyst and/or the polymerization inhibitor, an acid and/or an alkali for decomposing or removing the by-products, activated carbon for improving the color tone, diatomaceous earth for improving the filtration efficiency and filtration rate, and the like may be used.

The production method of the present invention can be repeatedly carried out. In other words, the catalyst recovery step of separating and recovering a solid containing the catalyst A and/or the catalyst B from the reaction system and the reaction step 2 of producing a (meth) acrylate by using the catalyst A and/or the catalyst B which have recovered can be repeatedly carried out.

EXAMPLES

Hereinafter, the present invention will be described more specifically with reference to Examples and Comparative Examples, but the present invention is not limited to these Examples. Incidentally, in the following description, the term "parts" means "parts by mass" and the term "%" means "% by mass" unless otherwise stated.

The reaction yield in Examples and Comparative Examples was calculated by using the result of quantitative determination of the monohydric alcohol (derived from the monofunctional (meth) acrylate used as a raw material) generated as a by-product as the transesterification reaction proceeded and the following formula. Incidentally, the quantitative determination of monohydric alcohol was conducted by using a high performance liquid chromatograph equipped with a differential refractive index detector (column: Atlantis (Part No. 186003748, column inner diameter: 4.6 mm, column length: 250 mm) manufactured by Nihon Waters K. K., solvent: pure water or 10% by volume aqueous solution of isopropanol) and the internal standard method.

Reaction yield (% by mole)=number of moles of monohydric alcohol generated as by-product as transesterification reaction proceeds/(number of moles of alcohol used as raw material×number of alcoholic hydroxyl groups in alcohol molecule used as raw material)×100

The purification yield in Examples and Comparative Examples was calculated by using the mass of the purified product which contained the target (meth) acrylate and was obtained after subjecting the reaction product after completion of the transesterification reaction to separation and purification operations such as distillation, crystallization, filtration, and the like.

Purification yield (%)=purified product containing target (meth) acrylate (parts)/(molecular weight of (meth) acrylate generated when all alcoholic hydroxyl groups in alcohol used as raw material are (meth) acrylated×number of moles of alcohol used as raw material)×100

In Examples and Comparative Examples, the confirmation that the target (meth) acrylate was contained in the reaction product and the purified product was performed by using a high performance liquid chromatograph equipped with a UV detector (column: ACQUITY UPLC BEH C18 (Part No. 186002350, column inner diameter: 2.1 mm, column length: 50 mm) manufactured by Nihon Waters K. K., detection wavelength: 210 nm, solvent: mixed solvent of 0.03% by mass aqueous solution of trifluoroacetic acid with methanol).

The analytical method of the solid which contains the catalyst A and/or the catalyst B and is separated and recovered in the catalyst recovery step of Examples will be described below.

$^1$H-NMR measurement was conducted by using AVANCE III manufactured by Bruker. The frequency was 400 MHz, the measurement temperature was 23° C., and deuterated DMSO was used as the measurement solvent.

CHN elemental analysis was conducted by using CHN coder MT-5 manufactured by Yanaco Technical Science Co., Ltd.

The content of Zn was analyzed by ICP atomic emission spectrometry using SPECTRO ARCOS SOP manufactured by AMETEK Inc.

Example 1

(Reaction Step 1 and Catalyst Recovery Step)

Into a 1 liter flask equipped with a stirrer, a thermometer, a gas introduction tube, a rectifying column, and a cooling tube, 69.33 parts (0.51 mole) of pentaerythritol, 690.05 parts (5.30 moles) of 2-methoxyethyl acrylate, 2.038 parts (0.018 mole) of DABCO as the catalyst A, 3.260 parts (0.018 mole) of zinc acetate as the catalyst B, and 1.56 parts (2036 ppm by mass with respect to the total mass of the raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 130 to 760 mmHg while heating and stirring the reaction liquid at a temperature in a range of from 105 to 120° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 88% after 30 hours from the start of heating and stirring, and thus the pressure in the reaction system was returned to normal pressure and taking out of the by-product was terminated as well as heating of the reaction liquid was terminated.

With regard to the reaction product thus obtained, the reaction liquid was cooled to room temperature as a catalyst recovery step, and 3.89 parts of solid was then separated through pressure filtration. The filtrate after filtration was subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains pentaerythritol triacrylate and pentaerythritol tetraacrylate as main components. The purification yield calculated by assuming the residue as a purified product was 96%. The results are presented in Table 1.

As a result of analysis of the solid obtained by separation through filtration in the catalyst recovery step accompanying the reaction step 1, it has been confirmed that the main component of the solid was a complex formed by DABCO of the catalyst A and a compound which contains zinc and is represented by the general formula (2) of the catalyst B at a proportion of 1:2 (molar ratio). The result of analysis and the structural formula (4) of the complex are described.

$^1$H-NMR analysis (deuterated DMSO): δ 6.03 ppm (m, 6H, CH$_2$=CHCO—), δ 5.55 ppm (m, 3H, CH$_2$=CHCO—), δ 2.85 ppm (s, 12H, N—CH$_2$CH$_2$—N), δ 1.78 ppm (s, 3H, CH$_3$CO—)

Elemental analysis: Calcd. for C$_{17}$H$_{24}$O$_8$N$_2$Zn$_2$: C, 39.64; H, 4.70; O, 24.85; N, 5.44; Zn, 25.38%. Found: C, 39.80; H, 4.80; O, 25.44; N, 5.70; Zn, 24.26%.

[Chemical formula 4]

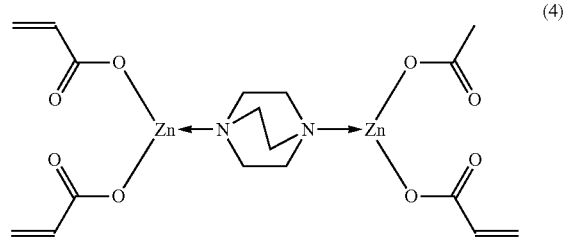

(4)

(Reaction Step 2 and Catalyst Recovery Step)

Into a 1 liter flask equipped with a stirrer, a thermometer, a gas introduction tube, a rectifying column, and a cooling tube, 69.33 parts (0.51 mole) of pentaerythritol, and 690.05 parts (5.30 moles) of 2-methoxyethyl acrylate, 1.233 parts (0.011 mole) of DABCO as the catalyst A, 0.625 parts (0.003 mole) of zinc acetate as the catalyst B, 3.699 parts (0.007 mole as catalyst A and 0.014 mole as catalyst B) of the solid obtained in the catalyst recovery step, and 1.56 parts (2035 ppm by mass with respect to the total mass of the raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 130 to 760 mmHg while heating and stirring the reaction liquid at a temperature in a range of from 105 to 120° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 89% after 30 hours from the start of heating and stirring, and thus the pressure in the reaction system was returned to normal pressure and taking out of the by-product was terminated as well as heating of the reaction liquid was terminated.

With regard to the reaction product thus obtained, the reaction liquid was cooled to room temperature as a catalyst recovery step, and 3.98 parts of solid was then separated through pressure filtration. The filtrate after filtration was subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains pentaerythritol triacrylate and pentaerythritol tetraacrylate as main components. The purification yield calculated by assuming the residue as a purified product was 97%. The results are presented in Table 1.

As a result of analysis of the solid obtained by separation through filtration in the catalyst recovery step accompanying the reaction step 2, it has been confirmed that the main component of the solid was a complex formed by DABCO of the catalyst A and a compound which contains zinc and is represented by the general formula (2) of the catalyst B at a proportion of 1:2 (molar ratio). The result of analysis and the structural formula (5) of the complex are described.

In addition, the results obtained by repeatedly carrying out the reaction step 2 and the catalyst recovery step by using the solid as a catalyst are presented in Table 1.

$^1$H-NMR analysis (deuterated DMSO): δ 6.03 ppm (m, 8H, $CH_2$=CHCO—), δ 5.55 ppm (m, 4H, $CH_2$=CHCO—), δ 2.85 ppm (s, 12H, N—$CH_2CH_2$—N)

Elemental analysis: Calcd. for $C_{18}H_{24}O_8N_2Zn_2$: C, 41.01; H, 4.59; O, 24.28; N, 5.31; Zn, 24.81%. Found: C, 41.18; H, 4.69; O, 24.86; N, 5.57; Zn, 23.71%.

[Chemical formula 5]

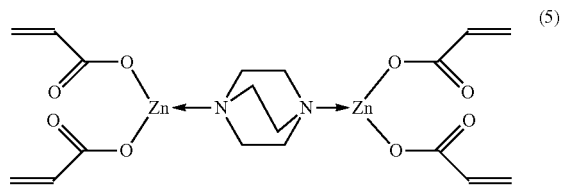

(5)

TABLE 1

| Number of reactions | Example 1 | Catalyst A | Catalyst B | Recovered catalyst | Main component of recovered catalyst | Reaction time (hr) | Reaction yield (%) | Purification yield (%) |
|---|---|---|---|---|---|---|---|---|
| 1 | Reaction step 1 and catalyst recovery step | DABCO: 2.038 parts (0.018 mole) | Zinc acetate: 3.260 parts (0.018 mole) | Unused | Structural Formula (4) | 30 | 88 | 96 |
| 2 | Reaction step 2 and catalyst recovery step | DABCO: 1.233 parts (0.011 mole) | Zinc acetate: 0.625 parts (0.003 mole) | 3.699 parts (0.007 mole as catalyst A and 0.014 mole as catalyst B) | Structural Formula (5) | 30 | 89 | 97 |
| 3 | Reaction step 2 and catalyst recovery step | DABCO: 1.233 parts (0.011 mole) | Zinc acetate: 0.625 parts (0.003 mole) | 3.786 parts (0.007 mole as catalyst A and 0.014 mole as catalyst B) | Structural Formula (5) | 30 | 88 | 96 |
| 4 | Reaction step 2 and catalyst | DABCO: 1.233 parts | Zinc acetate: | 3.786 parts (0.007 mole as catalyst A | Structural Formula (5) | 30 | 88 | 96 |

TABLE 1-continued

| Number of reactions | Example 1 | Catalyst A | Catalyst B | Recovered catalyst | Main component of recovered catalyst | Reaction time (hr) | Reaction yield (%) | Purification yield (%) |
|---|---|---|---|---|---|---|---|---|
| | recovery step | (0.011 mole) | 0.625 parts (0.003 mole) | and 0.014 mole as catalyst B | | | | |
| 5 | Reaction step 2 and catalyst recovery step | DABCO: 1.233 parts (0.011 mole) | Zinc acetate: 0.625 parts (0.003 mole) | 3.786 parts (0.007 mole as catalyst A and 0.014 mole as catalyst B) | Structural Formula (5) | 30 | 89 | 97 |

Example 2

(Reaction Step 1 and Catalyst Recovery Step)

Into a 1 liter flask equipped with a stirrer, a thermometer, a gas introduction tube, a rectifying column, and a cooling tube, 86.33 parts (0.34 mole) of dipentaerythritol, 690.05 parts (5.30 moles) of 2-methoxyethyl acrylate, 4.077 parts (0.036 mole) of DABCO as the catalyst A, 6.520 parts (0.036 mole) of zinc acetate as the catalyst B, and 1.63 parts (2061 ppm by mass with respect to the total mass of the raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 250 to 760 mmHg while heating and stirring the reaction liquid at a temperature in a range of from 120 to 145° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 86% after 24 hours from the start of heating and stirring, and thus the pressure in the reaction system was returned to normal pressure and taking out of the by-product was terminated as well as heating of the reaction liquid was terminated. With regard to the reaction product thus obtained, the reaction liquid was cooled to room temperature as a catalyst recovery step, and 8.38 parts of solid was then separated through pressure filtration. The filtrate after filtration was subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains dipentaerythritol pentaacrylate and dipentaerythritol hexaacrylate as main components. The purification yield calculated by assuming the residue as a purified product was 99%. The results are presented in Table 2.

As a result of analysis of the solid obtained by separation through filtration in the catalyst recovery step accompanying the reaction step 1, it has been confirmed that the main component of the solid was a complex formed by DABCO of the catalyst A and a compound which contains zinc and is represented by the general formula (2) of the catalyst B at a proportion of 1:2 (molar ratio). In addition, it has been confirmed that the complex has the structural formula (5).

(Reaction Step 2 and Catalyst Recovery Step)

Into a 1 liter flask equipped with a stirrer, a thermometer, a gas introduction tube, a rectifying column, and a cooling tube, 86.33 parts (0.34 mole) of dipentaerythritol, 690.05 parts (5.30 moles) of 2-methoxyethyl acrylate, 2.382 parts (0.021 mole) of DABCO as the catalyst A, 0.975 parts (0.005 mole) of zinc acetate as the catalyst B, 7.965 parts (0.015 mole as catalyst A and 0.030 mole as catalyst B) of the solid obtained in the catalyst recovery step, and 1.63 parts (2059 ppm by mass with respect to the total mass of raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 250 to 760 mmHg while heating and stirring the reaction liquid at a temperature in a range of from 120 to 145° C., and a liquid mixture of 2-methoxyethanol generated as a by-product and 2-methoxyethyl acrylate as the transesterification reaction proceeded was taken out from the reaction system via the rectifying column and the cooling tube. In addition, 2-methoxyethyl acrylate in the same parts by mass as that of the liquid taken out was added to the reaction system at all times. As a result of quantitative determination of 2-methoxyethanol contained in the liquid taken out from the reaction system, the reaction yield reached 87% after 24 hours from the start of heating and stirring, and thus the pressure in the reaction system was returned to normal pressure and taking out of the by-product was terminated as well as heating of the reaction liquid was terminated. With regard to the reaction product thus obtained, the reaction liquid was cooled to room temperature as a catalyst recovery step, and 8.38 parts of solid was then separated through pressure filtration. The filtrate after filtration was subjected to vacuum distillation for 8 hours at a temperature of from 70 to 95° C. and a pressure in a range of from 0.001 to 100 mmHg while allowing dry air to bubble in the filtrate, thereby separating a distillate containing unreacted 2-methoxyethyl acrylate. As a result of composition analysis of the residue after vacuum distillation using a high performance liquid chromatograph equipped with a UV detector, it has been confirmed that the residue contains dipentaerythritol pentaacrylate and dipentaerythritol hexaacrylate as main components. The purification yield calculated by assuming the residue as a purified product was 99%. The results are presented in Table 2.

As a result of analysis of the solid obtained by separation through filtration in the catalyst recovery step accompanying the reaction step 2, it has been confirmed that the solid contains the complex represented by the structural formula (5) as a main component in the same manner as the solid obtained by separation through filtration in the catalyst recovery step accompanying the reaction step 1. The results obtained by repeatedly carrying out the reaction step 2 and the catalyst recovery step by using the solid as a catalyst are presented in Table 2.

TABLE 2

| Number of reactions | Example 2 | Catalyst A | Catalyst B | Recovered catalyst | Main component of recovered catalyst | Reaction time (hr) | Reaction yield (%) | Purification yield (%) |
|---|---|---|---|---|---|---|---|---|
| 1 | Reaction step 1 and catalyst recovery step | DABCO: 4.077 parts (0.036 mole) | Zinc acetate: 6.520 parts (0.036 mole) | Unused | Structural Formula (5) | 24 | 86 | 99 |
| 2 | Reaction step 2 and catalyst recovery step | DABCO: 2.382 parts (0.021 mole) | Zinc acetate: 0.975 parts (0.005 mole) | 7.965 parts (0.015 mole as catalyst A and 0.030 mole as catalyst B) | Structural Formula (5) | 24 | 87 | 99 |
| 3 | Reaction step 2 and catalyst recovery step | DABCO: 2.382 parts (0.021 mole) | Zinc acetate: 0.975 parts (0.005 mole) | 7.965 parts (0.015 mole as catalyst A and 0.030 mole as catalyst B) | Structural Formula (5) | 24 | 86 | 98 |
| 4 | Reaction step 2 and catalyst recovery step | DABCO: 2.382 parts (0.021 mole) | Zinc acetate: 0.975 parts (0.005 mole) | 7.965 parts (0.015 mole as catalyst A and 0.030 mole as catalyst B) | Structural Formula (5) | 24 | 87 | 99 |
| 5 | Reaction step 2 and catalyst recovery step | DABCO: 2.382 parts (0.021 mole) | Zinc acetate: 0.975 parts (0.005 mole) | 7.965 parts (0.015 mole as catalyst A and 0.030 mole as catalyst B) | Structural Formula (5) | 24 | 86 | 98 |

Example 3

(Reaction Step 1 and Catalyst Recovery Step)

Into a 300 milliliter flask equipped with a stirrer, a thermometer, a gas introduction tube, a rectifying column, and a cooling tube, 85.00 parts (0.64 mole) of diethylene glycol monovinyl ether, 110.67 parts (1.29 moles) of methyl acrylate, 1.082 parts (0.010 mole) of DABCO as the catalyst A, 4.004 parts (0.019 mole) of zinc acrylate as the catalyst B, 0.053 parts (265 ppm by mass with respect to the total mass of raw materials charged) of hydroquinone monomethyl ether, and 0.025 parts (123 ppm by mass with respect to the total mass of the raw materials charged) of phenothiazine were charged, and an oxygen-containing gas (5% by volume of oxygen and 95% by volume of nitrogen) was allowed to bubble in the liquid. The reaction liquid was heated and stirred at a temperature in a range of from 85 to 105° C., and a liquid mixture of methanol and methyl acrylate generated as a by-product as the transesterification reaction proceeded was taken out from the reaction system via the rectifying column and the cooling tube. In addition, methyl acrylate in the same parts by mass as that of the liquid taken out was added to the reaction system at all times. As a result of quantitative determination of methanol contained in the liquid taken out from the reaction system, the reaction yield reached 90% after 25 hours from the start of heating and stirring, and thus the heating of the reaction liquid was terminated. With regard to the reaction product thus obtained, the reaction liquid was cooled to room temperature as a catalyst recovery step, and 4.32 parts of solid was then separated through pressure filtration. The filtrate after filtration was subjected to vacuum distillation for 8 hours at a temperature of from 70 to 80° C. and a pressure in a range of from 0.001 to 700 mmHg while allowing dry air to bubble in the filtrate, thereby separating a distillate containing unreacted methyl acrylate. As a result of composition analysis of the residue after vacuum distillation using a high performance liquid chromatograph equipped with a UV detector, it has been confirmed that the residue contains 2-(2-vinyloxyethoxy)ethyl acrylate as a main component. The purification yield calculated by assuming the residue as a purified product was 98%. The results are presented in Table 3.

As a result of analysis of the solid obtained by separation through filtration in the catalyst recovery step accompanying the reaction step 1, it has been confirmed that the main component of the solid was a complex formed by DABCO of the catalyst A and a compound which contains zinc and is represented by the general formula (2) of the catalyst B at a proportion of 1:2 (molar ratio). In addition, it has been confirmed that the complex has the structural formula (5).

(Reaction Step 2 and Catalyst Recovery Step)

Into a 300 milliliter flask equipped with a stirrer, a thermometer, a gas introduction tube, a rectifying column, and a cooling tube, 85.00 parts (0.64 mole) of diethylene glycol monovinyl ether, 110.67 parts (1.29 moles) of methyl acrylate, 0.195 parts (0.002 mole) of DABCO as the catalyst A, 0.721 parts (0.003 mole) of zinc acrylate as the catalyst B, 4.170 parts (0.008 mole as catalyst A and 0.016 mole as catalyst B) of the solid obtained in the catalyst recovery step, 0.053 parts (265 ppm by mass with respect to the total mass of the raw materials charged) of hydroquinone monomethyl ether, and 0.025 parts (123 ppm by mass with respect to the total mass of the raw materials charged) of phenothiazine were charged, and an oxygen-containing gas (5% by volume of oxygen and 95% by volume of nitrogen) was allowed to bubble in the liquid. The reaction liquid was heated and stirred at a temperature in a range of from 85 to 105° C., and a liquid mixture of methanol and methyl acrylate generated as a by-product as the transesterification reaction proceeded was taken out from the reaction system via the rectifying column and the cooling tube. In addition, methyl acrylate in the same parts by mass as that of the liquid taken out was added to the reaction system at all times. As a result of quantitative determination of methanol contained in the liquid taken out from the reaction system, the reaction yield reached 91% after 25 hours from the start of heating and stirring, and thus the heating of the reaction liquid was terminated. With regard to the reaction product thus obtained, the reaction liquid was cooled to room temperature as a catalyst recovery step, and 4.37 parts of solid was then separated through pressure filtration. The filtrate after filtration was subjected to vacuum distillation for 8 hours at a temperature of from 70 to 80° C. and a pressure in a range of from 0.001 to 700 mmHg while allowing dry air to bubble in the filtrate, thereby separating a distillate containing unreacted methyl acrylate. As a result of composition analysis of the residue after vacuum distillation using a high performance liquid chromatograph equipped with a UV detector, it has been confirmed that the residue contains 2-(2-vinyloxyethoxy)ethyl acrylate as a main component. The purification yield calculated by assuming the residue as a purified product was 98%. The results are presented in Table 3.

As a result of analysis of the solid obtained by separation through filtration in the catalyst recovery step accompanying the reaction step 2, it has been confirmed that the solid contains the complex represented by the structural formula (5) as amain component in the same manner as the solid obtained by separation through filtration in the catalyst recovery step accompanying the reaction step 1. The results obtained by repeatedly carrying out the reaction step 2 and the catalyst recovery step by using the solid as a catalyst are presented in Table 3.

be seen that the target (meth) acrylate can be obtained at a favorable yield without a decrease in catalyst performance even when the catalyst is recovered by an extremely simple filtration operation and the reaction step is repeatedly carried out by using the recovered catalyst. In addition, the total amount of the catalyst A and catalyst B required is significantly smaller as compared to a case in which the reaction step 1 is carried out five times without using the recovered catalyst but using only new catalysts A and B, and it can be thus seen that the production method of the present invention is an extremely economically advantageous method as compared to the prior art.

Comparative Example 1

(Reaction Step 1 and Catalyst Recovery Step)

Into a 1 liter flask equipped with a stirrer, a thermometer, a gas introduction tube, a rectifying column, and a cooling tube, 97.07 parts (0.71 mole) of pentaerythritol, 668.81 parts (5.14 moles) of 2-methoxyethyl acrylate, 2.479 parts (0.030 mole) of N-methylimidazole as the catalyst A, 6.155 parts (0.034 mole) of zinc acetate as the catalyst B and 1.22 parts (1573 ppm by mass with respect to the total mass of raw materials charged) of hydroquinone monomethyl ether were charged, and an oxygen-containing gas (5% by volume of oxygen and 95% by volume of nitrogen) was allowed to bubble in the liquid. The pressure in the reaction system was adjusted in a range of from 130 to 760 mmHg while heating and stirring the reaction liquid at a temperature in a range of from 105 to 120° C., and a liquid mixture of 2-methoxyethanol generated as a by-product and 2-methoxyethyl acrylate as the transesterification reaction proceeded was taken out from the reaction system via the rectifying column and

TABLE 3

| Number of reactions | Example 3 | Catalyst A | Catalyst B | Recovered catalyst | Main component of recovered catalyst | Reaction time (hr) | Reaction yield (%) | Purification yield (%) |
|---|---|---|---|---|---|---|---|---|
| 1 | Reaction step 1 and catalyst recovery step | DABCO: 1.082 parts (0.010 mole) | Zinc acrylate: 4.004 parts (0.019 mole) | Unused | Structural Formula (5) | 25 | 90 | 98 |
| 2 | Reaction step 2 and catalyst recovery step | DABCO: 0.195 parts (0.002 mole) | Zinc acrylate: 0.721 parts (0.003 mole) | 4.170 parts (0.008 mole as catalyst A and 0.016 mole as catalyst B) | Structural Formula (5) | 25 | 91 | 98 |
| 3 | Reaction step 2 and catalyst recovery step | DABCO: 0.195 parts (0.002 mole) | Zinc acrylate: 0.721 parts (0.003 mole) | 4.170 parts (0.008 mole as catalyst A and 0.016 mole as catalyst B) | Structural Formula (5) | 25 | 90 | 98 |
| 4 | Reaction step 2 and catalyst recovery step | DABCO: 0.195 parts (0.002 mole) | Zinc acrylate: 0.721 parts (0.003 mole) | 4.170 parts (0.008 mole as catalyst A and 0.016 mole as catalyst B) | Structural Formula (5) | 25 | 90 | 98 |
| 5 | Reaction step 2 and catalyst recovery step | DABCO: 0.195 parts (0.002 mole) | Zinc acrylate: 0.721 parts (0.003 mole) | 4.170 parts (0.008 mole as catalyst A and 0.016 mole as catalyst B) | Structural Formula (5) | 25 | 91 | 98 |

The results obtained by repeatedly carrying out the reaction step and the catalyst recovery step accompanying the reaction step five times in Examples are presented, and it can the cooling tube. In addition, 2-methoxyethyl acrylate in the same parts by mass as that of the liquid taken out was added to the reaction system at all times. As a result of quantitative and determination of 2-methoxyethanol contained in the liquid taken out from the reaction system, the reaction yield reached 89% after 20 hours from the start of heating and stirring, and thus the pressure in the reaction system was returned to normal pressure and taking out of the by-product was terminated as well as heating of the reaction liquid was terminated.

With regard to the reaction product thus obtained, the reaction liquid was cooled to 5° C. as a catalyst recovery step, but the formation of solid was not confirmed. To the reaction liquid, 100 g of n-hexane was further added, but the formation of solid was not still confirmed, and thus it was not able to recover the catalyst.

Comparative Examples 2 and 3

The reaction step 1 and the catalyst recovery step were carried out in the same manner as in Comparative Example 1 except that the catalyst A and the catalyst B were changed. The transesterification reaction proceeded in the reaction step 1, but the formation of solid was not confirmed in the catalyst recovery step, and thus it was not able to recover the catalyst. The results are presented in Table 4.

TABLE 4

| | Catalyst A | Catalyst B | Reaction yield (%) | Amount of catalyst recovered |
|---|---|---|---|---|
| Example 1 | DABCO: 2.038 parts | Zinc acetate: 3.260 parts | 88 | 3.89 parts |
| Comparative Example 1 | N-methyl-imidazole: 2.479 parts | Zinc acetate: 6.155 parts | 89 | Not able to recover |
| Comparative Example 2 | N,N-dimethyl-4-aminopyridine: 3.688 parts | Zinc acetate: 6.155 parts | 86 | Not able to recover |
| Comparative Example 3 | Triphenyl-phosphine: 4.767 parts | Zinc acetylacetonate: 4.683 parts | 94 | Not able to recover |

INDUSTRIAL APPLICABILITY

According to the method of the present invention, it is possible to obtain a (meth) acrylate from an alcohol and a monofunctional (meth) acrylate at a favorable yield. It is possible to suitably use the (meth) acrylate obtained by the method of the present invention in various kinds of industrial applications as a crosslinking component of blended materials such as paints, inks, adhesives, optical lenses, fillers, and molding materials or a reactive diluent component.

The invention claimed is:

1. A method for producing a (meth)acrylate, the method comprising the following steps:
   (reaction step 1) a step of producing a (meth)acrylate by subjecting an alcohol and a monofunctional (meth) acrylate to a transesterification reaction using the following catalyst A and the following catalyst B concurrently:
   catalyst A: one or more kinds of compounds selected from the group consisting of a cyclic tertiary amine having an azabicyclo structure, a salt of the cyclic tertiary amine, and a complex of the cyclic tertiary amine,
   catalyst B: one or more kinds of compounds selected from the group consisting of a compound containing zinc;
   (catalyst recovery step) a step of separating a solid containing the catalyst A and/or the catalyst B from a reaction product which is obtained in the reaction step 1 and contains a (meth)acrylate; and
   (reaction step 2) a step of producing a (meth)acrylate by subjecting an alcohol and a monofunctional (meth) acrylate to a transesterification reaction using the solid which is recovered in the catalyst recovery step and contains the catalyst A and/or the catalyst B as a catalyst or a part of a catalyst.

2. The method for producing a (meth)acrylate according to claim 1, wherein the alcohol is a polyhydric alcohol having three or more alcoholic hydroxyl groups.

3. The method for producing a (meth)acrylate according to claim 1, wherein the alcohol is any of trimethylolethane, trimethylolpropane, glycerin, an alkylene oxide adduct of glycerin, tris (2-hydroxyethyl)isocyanurate, triethanolamine, ditrimethylolethane, ditrimethylolpropane, diglycerin, an alkylene oxide adduct of diglycerin, pentaerythritol, an alkylene oxide adduct of pentaerythritol, xylitol, dipentaerythritol, an alkylene oxide adduct of dipentaerythritol, D-sorbitol, or polyglycerin.

4. The method for producing a (meth)acrylate according to claim 1, wherein the alcohol is pentaerythritol or dipentaerythritol.

5. The method for producing a (meth)acrylate according to claim 1, wherein the monofunctional (meth)acrylate is any of methyl acrylate, ethyl acrylate, n-butyl acrylate, i-butyl acrylate, or 2-methoxyethyl acrylate.

6. The method for producing a (meth)acrylate according to claim 1, wherein the monofunctional (meth)acrylate is 2-methoxyethyl acrylate.

7. The method for producing a (meth)acrylate according to claim 1, wherein the catalyst A is any of quinuclidine, 3-hydroxyquinuclidine, triethylenediamine, or 2-(hydroxymethyl)triethylenediamine.

8. The method for producing a (meth)acrylate according to claim 1, wherein the catalyst B is a compound which contains zinc and is represented by the following general formula (2) or the following general formula (3):

[Chemical formula 1]

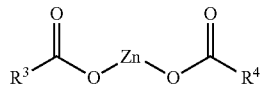

(2)

(wherein, $R^3$ and $R^4$ may be the same as or different from each other, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent; however, $R^3$ and $R^4$ do not have a halogen atom);

[Chemical formula 2]

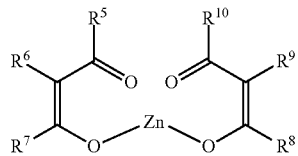

(3)

(wherein, $R^5$, $R^6$, $R^7$, $R^8$, $R^9$, and $R^{10}$ may be the same as or different from one another, are a linear or branched alkyl group having from 1 to 20 carbon atoms, a linear or branched alkenyl group having from 1 to 20 carbon atoms, an aryl group having from 6 to 24 carbon atoms, or a cycloalkyl group having from 5 to 20 carbon atoms, and may have a substituent; $R^6$ and $R^9$ may be a hydrogen atom).

9. The method for producing a (meth)acrylate according to claim 1, wherein the catalyst A is triethylenediamine and the catalyst B is a compound which contains zinc and is represented by the general formula (2).

\* \* \* \* \*